United States Patent
Matsukata et al.

(10) Patent No.: US 9,944,576 B2
(45) Date of Patent: Apr. 17, 2018

(54) METHOD FOR SEPARATING STRAIGHT-CHAIN CONJUGATED DIENE

(71) Applicants: Waseda University, Tokyo (JP); JXTG Nippon Oil & Energy Corporation, Tokyo (JP)

(72) Inventors: Masahiko Matsukata, Tokyo (JP); Motomu Sakai, Tokyo (JP); Yasuhito Sasaki, Tokyo (JP); Tatsuo Hamamatsu, Tokyo (JP); Nobuhiro Kimura, Tokyo (JP)

(73) Assignees: WASEDA UNIVERSITY, Tokyo (JP); JXTG Nippon Oil & Energy Corporation, Tokyo (JP)

( * ) Notice: Subject to any disclaimer, the term of this patent is extended or adjusted under 35 U.S.C. 154(b) by 0 days.

(21) Appl. No.: 15/537,063

(22) PCT Filed: Sep. 30, 2015

(86) PCT No.: PCT/JP2015/077690
§ 371 (c)(1),
(2) Date: Jun. 16, 2017

(87) PCT Pub. No.: WO2016/098417
PCT Pub. Date: Jun. 23, 2016

(65) Prior Publication Data
US 2017/0349510 A1    Dec. 7, 2017

(30) Foreign Application Priority Data

Dec. 19, 2014 (JP) .................................. 2014-257055

(51) Int. Cl.
*C07C 7/144* (2006.01)
*B01D 69/10* (2006.01)
(Continued)

(52) U.S. Cl.
CPC ............ *C07C 7/144* (2013.01); *B01D 53/228* (2013.01); *B01D 69/10* (2013.01); *B01D 69/12* (2013.01);
(Continued)

(58) Field of Classification Search
None
See application file for complete search history.

(56) References Cited

U.S. PATENT DOCUMENTS 9,856,190 B2 *   1/2018   Kishida ................... C07C 7/12
2004/0033370 A1  2/2004   Chau et al.
(Continued)

FOREIGN PATENT DOCUMENTS

JP    536515 B1    2/1961
JP    S36515 B1    2/1961
(Continued)

OTHER PUBLICATIONS

Int'l Search Report dated Dec. 15, 2015 in Int'l Application No. PCT/JP2015/077690.
(Continued)

*Primary Examiner* — Tam M Nguyen
(74) *Attorney, Agent, or Firm* — Panitch Schwarze Belisario & Nadel LLP

(57) ABSTRACT

The present invention provides a method for selectively separating a straight-chain conjugated diene with high purity from a mixture containing the straight-chain conjugated diene and at least one type of straight-chain olefin. The method involves separating the straight-chain conjugated diene from the mixture containing the straight-chain conjugated diene and the straight-chain olefin using a zeolite membrane composite. The composite contains a porous
(Continued)

support and a zeolite layer formed on the surface and in the fine pores of the support, and the zeolite contains an alkali metal cation.

10 Claims, 1 Drawing Sheet

(51) Int. Cl.
| | | |
|---|---|---|
| *B01D 69/12* | (2006.01) | |
| *B01D 71/02* | (2006.01) | |
| *B01D 53/22* | (2006.01) | |
| *C07C 7/13* | (2006.01) | |
| *C01B 39/22* | (2006.01) | |
| *C01B 39/38* | (2006.01) | |

(52) U.S. Cl.
CPC ............ *B01D 71/028* (2013.01); *C01B 39/22* (2013.01); *C01B 39/38* (2013.01); *C07C 7/13* (2013.01)

(56) References Cited

U.S. PATENT DOCUMENTS

| | | | |
|---|---|---|---|
| 2008/0035566 A1* | 2/2008 | Sabottke | B01D 61/246 |
| | | | 210/640 |
| 2008/0035567 A1* | 2/2008 | Sabottke | B01D 61/362 |
| | | | 210/640 |
| 2015/0232397 A1 | 8/2015 | Kishida et al. | |
| 2016/0159823 A1* | 6/2016 | Kishida | B01D 53/228 |
| | | | 585/830 |

FOREIGN PATENT DOCUMENTS

| | | |
|---|---|---|
| JP | 200426643 A | 1/2004 |
| JP | 2015174081 A | 10/2015 |
| WO | 2014045967 A1 | 3/2014 |
| WO | 2015141686 A1 | 9/2015 |

OTHER PUBLICATIONS

Matsukata et al, "Tanka Suiso Iseitai Bunri-yo Kanjo Silicalite-1 Maku Choseiho No Kento," Dai 28 Kai Zeolite Kenkyu Happyokai Koen Yokoshu, pp. 65, C4, (Nov. 29, 2012).

Matsukata et al, "Alpha-Alumina Kanjo Shijitaijo Eno Random Haiko silicalite-1 Maku No Choseiho No Kento," Abstracts of 34th Annual Meeting of Membrane Society of Japan, pp. 89, p-21 S (Apr. 27, 2012).

Sakai et al, "Silicalite-1 Maku O Mochiita Chosa Chokusa Alkane No Bunri," Asahikawa Taikai Tokubetsu Koen Kicho Irai Koen 44th Petroleum Petrochemical Symposium of JPI, pp. 36, 1A12 (Oct. 16, 2014).

Sakai et al, "Separation Property of Silicalite-1 Membrane for C10 Hydrocarbons," Kitakyushu Taikai Tokubetsu Koen Kicho Irai Koen 43rd Petroleum Petrochemical Symposium of JPI, pp. 78, 1B05 (Nov. 14, 2013).

Matsukata et al, "Kanjo Silicalite-1 Maku Ni Yoru Hexane Iseitai Bunri Kyodo No Kento," The Society of Chemical Engineerings, Japan Yokohama Taikai Kenkyu Happo Koen Yoshishu, pp. 102, p. 177 (Jul. 30, 2012).

* cited by examiner

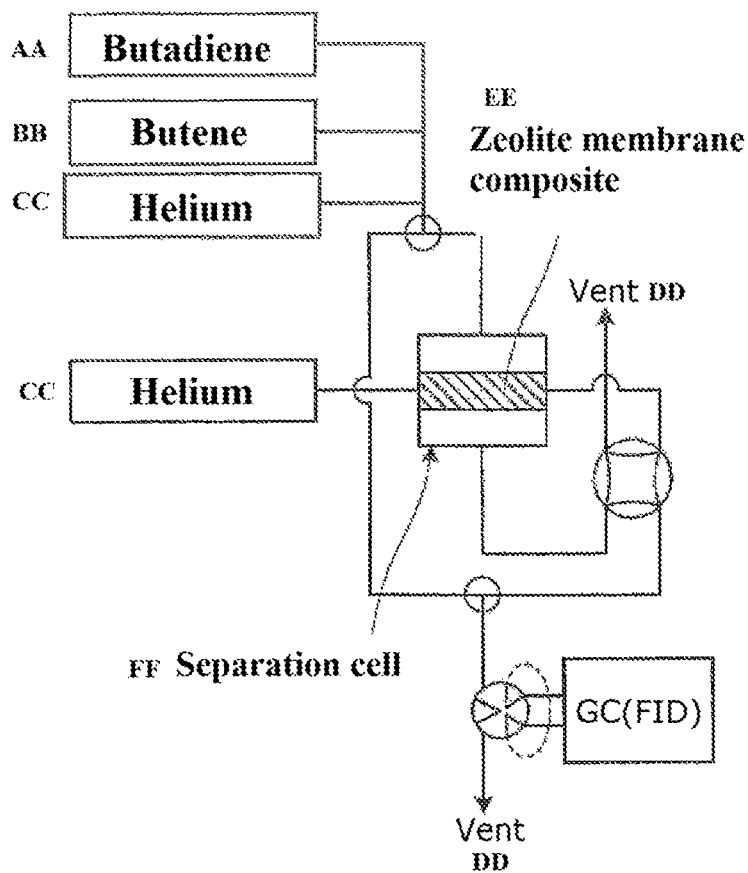
AA Butadiene
BB Butene
CC Helium
DD Vent
EE Zeolite membrane composite
FF Separation cell

METHOD FOR SEPARATING STRAIGHT-CHAIN CONJUGATED DIENE

CROSS-REFERENCE TO RELATED APPLICATION

This application is a Section 371 of International Application No. PCT/JP2015/077690, filed Sep. 30, 2015, which was published in the Japanese language on Jun. 23, 2016 under International Publication No. WO 2016/098417 A1, and the disclosure of which is incorporated herein by reference.

TECHNICAL FIELD

The present invention relates to a method for separating a straight-chain conjugated diene with an inorganic membrane.

BACKGROUND ART

The straight-chain conjugated diene is a useful compound, for example as a starting material for producing synthetic rubber or an intermediate of very large number of compounds. For example, butadiene is a main raw material of styrene-butadiene rubber, nitrile-butadiene rubber, and ABS resin. In addition, butadiene has been used for synthesis of adiponitrile that is a precursor of nylon synthesis as well as synthesis of chloroprene that is a precursor of chloroprene rubber, sulfolane that is used as a solvent and 1,4-butanediol that is important as a synthetic intermediate.

A straight-chain conjugated diene is generally produced through naphtha cracking or olefin dehydrogenation. Through these manufacturing methods, the straight-chain conjugated diene is produced as one component of the reaction mixture. Conventionally, separation and condensation of some ingredients from a mixture of gases or liquids containing organics has been carried out by distillation, azeotropic distillation, solvent extraction/distillation, or with an adsorbent, depending on the properties of the intended substances. However, these methods have drawbacks that a large amount of energy is required or the applicable scope of objects intended to be separated and condensed is restrictive.

An alternative to these methods has been proposed, which is membrane separation and condensation using a polymer membrane or an inorganic membrane, but the polymer membrane has a problem that it is deteriorated in performance due to heat, chemical substances or pressure.

Consequently, various inorganic membranes have been proposed, which are excellent in chemical resistance, oxidation resistance, heat resistant stability, and pressure resistance. Among them, a zeolite membrane has been expected to exhibit high separation performances.

Crystalline alumino-silicate generally termed as zeolite, has fine spaces of molecular sizes (nano-space) in one crystal and is referred to as "molecular sieve". There exist many types such as LTA (A-type), MFI (ZSM-5-type), MOR, FER, FAU (X-type, Y-type) and the like classified by their crystalline structures. Zeolites with such peculiar higher-order structures, perform a shape-selective function (molecular sieve function), an adsorption separation refining function, an ion exchange function, a solid acid function, and a catalyst function and thus are used in a wide variety of industrial fields.

In the case of using a zeolite membrane for separation and condensation, a zeolite membrane composite having a zeolite formed into a membrane on a support is usually used. A separation method using a zeolite membrane composite is known to be able to separate straight-chain butane (n-butane) and side-chain butane (isobutane) that are hydrocarbon isomers having 4 carbon atoms (see Patent Literature 1).

CITATION LIST

Patent Literature

Patent Literature 1: Japanese Patent Application Laid-Open Publication No. 2004-026643

SUMMARY OF INVENTION

Technical Problem

A straight-chain conjugated diene has uses as high-value-added products and although a method for separation thereof from a mixture containing it and an olefin and the like has been demanded, a method for separating a straight-chain conjugated diene, which can be industrially produced as a mixture with an olefin and the like with an inorganic membrane has not been established yet.

The present invention has been made in order to solve the above-described problems and has an object to provide a method for separating efficiently a straight-chain conjugated diene from a mixture comprising the straight-chain conjugated diene and a straight-chain olefin using a zeolite membrane composite which has high separation properties and permeability and whose zeolite can be easily formed into a membrane.

Solution to Problem

After extensive studies and researches made by the inventors, the present invention has been accomplished on the basis of a finding that a zeolite membrane composite comprising a porous support and a zeolite layer containing an alkali metal allows selectively a straight-chain conjugated diene to permeate therethrough from a mixture of the straight-chain conjugated diene and a straight-chain olefin.

That is, the present invention relates to a method for separating a straight-chain conjugated diene comprising separating the straight-chain conjugated diene from a mixture of the straight-chain conjugated diene and at least one type of straight-chain olefin using a zeolite membrane composite comprising a porous support and a zeolite layer formed on the surface and in the fine pores of the support, the zeolite containing an alkali metal as a cation.

The present invention also relates to the method for separating a straight-chain conjugated diene wherein the zeolite comprises a faujasite type zeolite.

The present invention also relates to the method for separating a straight-chain conjugated diene wherein the alkali metal is at least one type selected from Na, K, Rb and Cs.

The present invention also relates to the method for separating a straight-chain conjugated diene wherein the alkali metal consists of Na and Cs.

The present invention also relates to the method for separating a straight-chain conjugated diene wherein the Cs/Na molar ratio of the alkali metal is from 0.1 to 1.5 mol/mol.

The present invention also relates to the method for separating a straight-chain conjugated diene wherein the straight-chain conjugated diene is butadiene.

The present invention also relates to the method for separating a straight-chain conjugated diene wherein the zeolite membrane composite has a 1,3-butadiene/1-butene separation coefficient of 1.4 or greater at 60° C.

The present invention also relates to the method for separating a straight-chain conjugated diene wherein the faujasite type zeolite is a Y-type zeolite.

The present invention also relates to the method for separating a straight-chain conjugated diene wherein the separation is carried out in coexistence of an inorganic gas with the mixture.

The present invention also relates to the method for separating a straight-chain conjugated diene wherein the inorganic gas is at least one type selected from helium, argon, nitrogen, hydrogen, carbon monoxide, carbon dioxide and oxygen.

Advantageous Effect of Invention

The separation method according to the present invention makes it possible to obtain a straight-chain conjugated diene at a high purity and efficiency from a mixture of the straight-chain conjugated diene and at least one type of straight-chain olefin.

BRIEF DESCRIPTION OF DRAWING

FIG. 1 is a schematic view of a vapor permeation apparatus using a zeolite membrane composite used in the present invention.

DESCRIPTION OF EMBODIMENTS

The present invention will be described in detail below.

The porous support used in the present invention may be any porous inorganic substance as long as it is so chemically stable that a zeolite can be crystallized in the form of a membrane on the surface and in the pores of the substance. Specific examples of the support include sintered bodies of ceramic such as silica, α-alumina, γ-alumina, mullite, zirconia, titania, yttria, silicon nitride, and silicon carbide, sintered bodies of metals such as iron, bronze and stainless-steel, and molded bodies of glass and carbon. Among these, a sintered body of ceramic such as α-alumina and a sintered body of metal such as stainless-steel are preferably used from the viewpoint of heat resistance, mechanical strength, chemical resistance and easy production of a support and availability.

No particular limitation is imposed on the shape of the porous support if it can effectively separate a straight-chain conjugated diene from a mixture containing the same. For example, the support may be in the form of a flat-plate or tube or may have a honeycomb-shape with a large number of circular or square shaped tube-like pores, or may be monolithic.

No particular limitation is imposed on the average pore diameter of the porous support, which is, however, preferably is adjusted in pore diameter and is usually 0.02 μm or larger, preferably 0.05 μm or larger, more preferably 0.1 μm or larger and usually 20 μm or smaller, preferably 10 μm or smaller, more preferably 5 μm or smaller. If the porous support has a too small average pore diameter, it is likely to be small in the permeation amount while if it has a too large average pore diameter, it would be insufficient in the strength thereof and a zeolite membrane is unlikely to be precisely formed. The average pore diameter is, therefore, preferably 0.02 μm or larger and 20 μm or smaller.

In the present invention, the average pore diameter of the porous support was determined by a mercury intrusion method.

The outline of the mercury intrusion method is as described below.

The pore distribution of a porous support was determined from an intrusion curve obtained by a mercury intrusion method in the range of 3.7 kPa (corresponding to a pore diameter of 404 μm) and 414 MPA (corresponding to a pore diameter of 0.0036 μm) after subjecting the support to a decompression treatment under reduced pressure (50 μmHg or lower) for 10 minutes. From this intrusion curve obtained by mercury intrusion, D50 (pore diameter at a point when the total pore volume derived by integration from the largest pore diameter reaches 50 percent of the whole pore volume) is determined and defined as the average pore diameter.

No particular limitation is imposed on the porosity of the porous support, which may not be particularly required to be adjusted but is usually 20% or more and preferably 60% or less. The porosity affects the permeation flow rate upon separation of gas or liquid and if the porosity is too small, it tends to inhibit the permeated product from dispersing while if the porosity is too large, it tends to cause the support to be deteriorated in strength, Therefore, the porosity is preferably in the above range.

In the present invention, the porosity of the porous support was determined by a mercury intrusion method.

The zeolite membrane composite referred herein is a composite in which a zeolite layer is fixed and formed in the form of a membrane on the surface of and in the pores of the porous support, and for example such a composite produced by crystallizing a zeolite in the form of a membrane on the surface of a porous support by hydrothermal synthesis or steam treatment may be used.

In the present invention, the zeolite fixed in the form of a membrane in the zeolite membrane composite is referred to as "zeolite membrane".

The method for forming a zeolite into membrane over a porous support is preferably carried out by attaching a zeolite seed crystal over the porous support and then forming it into membrane by hydrothermal synthesis. In order to attach a zeolite seed crystal on a porous support, it is preferred that a dispersion liquid produced by dispersing zeolite seed crystal powder in a solvent is coated on the porous support. Alternatively, a zeolite seed crystal may be attached over a porous support by mixing zeolite seed crystal powder as a part of the raw materials of the support upon production thereof. The coating may be carried out by simply dropping a dispersion liquid containing a zeolite seed crystal over a porous support or alternatively, the support may be immersed into a dispersion liquid containing a zeolite seed crystal. Alternatively, a method that has been generally used, such as spin-coating, spray-coating, roll-coating, coating of a slurry, or filtration may also be used. With the objective of controlling the amount of a seed crystal to be attached over a porous support reproducibly, a method is preferably used, wherein a dispersion liquid containing a zeolite seed crystal is prepared and a porous support is immersed in the dispersion liquid.

The zeolite seed crystal used in the present invention may be any of those that are commercially available or may be produced from raw materials. When it is produced from raw materials, for example it can be produced by a conventional method using a silica source such as sodium silicate, silica gel, silica sol or silica powder, an alumina source such as sodium aluminate or aluminum hydroxide, a structure directing agent such as tetrapropylammonium hydroxide (TPAOH) or tetrapropylammonium methylmercuric (TPABr), and a mineralizer such as sodium hydroxide.

When a commercially available zeolite seed crystal is used, it is crushed with a pulverizer to a desired size and dispersed in water to prepare a dispersion liquid. The dispersion liquid thus prepared is arbitrarily attached to a porous support by any of the above-described methods. The dispersion liquid may be of any form such as slurry, sol, or solution and may be appropriately prepared depending on the coating method to be employed. When a method is employed, in which a porous support is immersed in a zeolite seed crystal dispersion liquid to be attached thereon, the dispersion liquid is preferably a slurry dispersion liquid because of easiness of attachment.

The amount of a zeolite seed crystal to be attached on a porous support, is preferably from 0.5 to 20 g/m$^2$, particularly preferably from 1 to 10 g/m$^2$. The amount of a zeolite seed crystal to be attached on a porous support within the above range can reduce the ratio of fines pores that are larger in diameter than the fine pores derived from the crystalline structure of the zeolite. It is necessary to decrease the number of fine pores having larger diameters than the fine pores derived from the crystalline structure of the zeolite as many as possible because they have no permeation selectivity.

In the present invention, the amount of a zeolite seed crystal attached to a porous support is obtained from the difference between the weights of the support before and after the zeolite seed crystal is attached.

The porous support having the zeolite seed crystal produced by the above-described method attached thereto is subjected to hydrothermal synthesis thereby forming a zeolite membrane on the porous support.

In the present invention, a general method may be used for forming a zeolite membrane by hydrothermal synthesis, but for example, a silica source, an aluminum source, a mineralizer, and a structure directing agent are mixed in water or an alcohol aqueous solution to produce a precursor solution, and a porous support having a zeolite seed crystal attached thereto may be immersed in the resulting precursor solution and subjected to hydrothermal synthesis by heating with an autoclave.

The temperature for hydrothermal synthesis is for example preferably from 20 to 200° C., more preferably from 50 to 100° C. If the temperature is too low, crystallization of a zeolite is unlikely to proceed while if the temperature is too high, the thickness of the resulting membrane would be too large due to the excess growth of a zeolite (i.e., permeation flow rate is decreased). The temperature is thus preferably within the above range.

The hydrothermal synthesis time is preferably from 6 to 168 hours, more preferably from 6 to 48 hours. If the time is too short, crystallization of the zeolite is unlikely to proceed while the time is too long, the thickness of the resulting membrane would be too large due to the excess growth of the zeolite (i.e., permeation flow rate is decreased). The time is thus preferably within the above range.

Although no particular limitation is imposed on the raw material constituting the above precursor solution, an amorphous silica, a fumed silica, a colloidal silica, tetraethylorthosilicate (TEOS), sodium silicate, potassium silicate, or lithium silicate may be used as a silica source, and sodium aluminate, potassium aluminate, aluminum chloride, aluminum nitrate, aluminum sulfate, or aluminum hydroxide may be used as an aluminum source.

A structure directing agent may be selected from various types depending on the desired zeolite, but for an MFI type zeolite, for example TPAOH and TPABr are preferably used. Depending on the type of zeolite to be intended, for example, an alkali metal or alkaline earth metal hydroxide may be used as a mineralizer, and specifically, sodium hydroxide and potassium hydroxide are preferably used.

An inorganic binder such as silica, alumina, an organic such as a polymer, or a silylation agent for modifying the zeolite surface may be contained as components constituting the zeolite membrane other than the zeolite if necessary. The zeolite membrane may partially contain an amorphous component but is preferably a zeolite membrane constituted substantially only by a zeolite.

No particular limitation is imposed on the thickness of the zeolite membrane, which is however, usually 0.1 µm or larger, preferably 0.6 µm or larger, more preferably 1.0 µm or larger and usually 100 µm or smaller, preferably 60 µm or smaller, more preferably 20 µm or smaller. If the zeolite membrane is too thick, it tends to be decreased in the permeation amount while if the zeolite membrane is too thin, it tends to be degraded in the selectivity and membrane strength. Therefore, the thickness is preferably within the above range.

In the present invention, the thickness of the zeolite membrane was determined with a field emission scanning electron microscope.

No particular limitation is imposed on the particle diameter of the zeolite constituting the zeolite membrane. However, if it is too small, the grain boundary tends to be large and thus to decrease the permeation selectivity. Therefore, it is usually 30 nm or larger, preferably 50 nm or larger, more preferably 100 nm or larger and the upper limit is equal to or smaller than the membrane thickness, for example, 100 µm or smaller, preferably 60 µm or smaller, more preferably 20 µm or smaller, particularly preferably the same as the zeolite membrane thickness. When the particle diameter of a zeolite is equal to the thickness of the zeolite membrane, the zeolite has the smallest grain boundary. The zeolite membrane produced through hydrothermal synthesis is preferable because the particle diameter of the zeolite can be equal to the thickness of the zeolite membrane.

In the present invention, the particle diameter of a zeolite was determined with a field emission scanning electron microscope.

In the present invention, the zeolite is preferably a faujasite type zeolite. The faujasite type zeolite is a zeolite represented by FAU structure in accordance with the skeletal structure types defined by the IUPAC recommendations. The faujasite zeolite may contain zeolites other than the faujasite zeolite to an extent that the advantageous effects of the present invention are not impaired. The zeolite that is a faujasite type has a high permeability derived from the three-dimensional large pores.

The faujasite type zeolite is preferably an X-type zeolite or Y-type zeolite, particularly preferably a Y-type zeolite. The faujasite type zeolite that is a Y-type zeolite has a high alkali metal concentration in the skeleton.

The zeolite used in the present invention contains an alkali metal as a cation. The alkali metal can be included as a cation in raw materials for synthesizing a zeolite or by a method such as ion exchange of a zeolite. A zeolite has a strong affinity with a straight-chain conjugated diene with a large polarity due to inclusion of an alkali metal.

The alkali metal is preferably at least one type selected from Na, K, Rb and Cs. Hereinafter, in accordance with the conventional method, for example X-type zeolite wherein the cation of zeolite is Na is designated as Na X-type zeolite, and Y-type zeolite wherein the cation is Na is designated as Na Y-type zeolite. An alkali metal that is at least one type selected from Na, K, Rb and Cs is effective while an alkali metal that is a combination of two types such as Na and Cs is particularly effective.

When two types of alkali metals such as Na and Cs are used, the molar ratio of CS/Na is preferably from 0.1 to 1.5 mol/mol, more preferably 0.3 to 0.6 mol/mol.

The alkali metal content in the zeolite is preferably from 5 to 60 percent by mass, more preferably from 10 to 50 percent by mass. If the content is less than 5 percent by mass, the resulting composite may be deteriorated in selectivity while if the content is more than 60 percent by mass, the alkali metal or salt thereof may precipitate.

No particular limitation is imposed on the shape of the zeolite membrane composite used in the present invention, which may, therefore, be of any shape such as tubular, hollow treads, monolith, and honeycomb types. No particular limitation is imposed on the size, either. For example, when the composite is tubular, the composite having a length of 2 cm or longer and 200 cm or shorter, an inner diameter of 0.05 cm or larger and 2 cm or smaller and a thickness of 0.5 mm or larger and 4 mm or smaller is practical and thus preferable.

The present invention relates to a method for separating selectively a straight-chain conjugated diene from a mixture of the straight-chain conjugated diene and at least one type of straight-chain olefin using the above-described zeolite membrane composite.

The method for separating a straight-chain conjugate diene according to the present invention is preferably used for separation of a straight-chain conjugated diene having 4 to 6 carbon atoms, for example butadiene, piperylene, 1,3-hexadiene, and 2,4-hexadiene. Specifically, the method can be suitably used for separation of a straight-chain conjugated diene from a mixture containing the straight-chain conjugated diene and at least one type of straight-chain olefin, such as a reaction mixture resulting from a process for producing a diene by dehydrogenation of C4 to C6 fractions or an olefin having 4 to 6 carbon atoms produced in a naphtha cracker or naphtha catalytic cracker.

For example, butadiene is generally produced by naphtha cracking or dehydrogenation of butene. In these methods, butadiene is produced as one component of a mixture, which contains butadiene that is a straight-chain conjugated diene and 1-butene that is a straight-chain olefin. The method for separating a straight-chain conjugate diene of the present invention can selectively separate even a straight-chain conjugated diene and a straight-chain olefin that cannot be separated with the shape-selective function of a zeolite and thus can selectively separate butadiene from the above-described mixture containing butadiene and a straight-chain olefin.

In the present invention, the content of a straight-chain conjugated diene in a mixture containing the straight-chain conjugated diene and at least one type of straight-chain olefin is preferably 1 percent by mass or more, more preferably 10 percent by mass or more, more preferably 25 percent by mass or more. If the content of the straight-chain conjugated diene is less than 1 percent by mass, a large number of steps might be needed even if multi-step separation membrane separation is used.

Examples of the straight-chain olefin include straight-chain monoolefins and straight-chain diolefins other than straight-chain conjugated dienes, but straight-chain monoolefins are preferable.

In the present invention, the mixture having 4 to 6 carbon atoms containing a straight-chain conjugated diene and at least one type of straight-chain olefin may contain a hydrocarbon having 4 to 6 carbon atoms other than the straight-chain olefin.

Among the hydrocarbons having 4 to 6 carbon atoms, a straight-chain paraffin can be separated from a straight-chain conjugated diene more easily than a straight-chain olefin. This is because the difference in adsorptivity between the straight-chain paraffin and the straight-chain conjugated diene is considered to be larger than the difference in adsorptivity between the straight-chain olefin and the straight-chain conjugated diene. Since among the hydrocarbons having 4 to 6 carbon atoms, branched components such as isoparaffin, isoolefin and the like or components having a ring structure that is a cyclo-ring or an aromatic ring are different in the hydrocarbon backbone from the straight-chain conjugated diene, the zeolite membrane composite used in the present invention can separate a straight-chain conjugated diene from these components.

In the method of separating a straight-chain conjugated diene selectively from a mixture containing the straight-chain conjugated diene and at least one type of straight-chain olefin according to the present invention, the method is preferably carried out in coexistence of an inert gas as a dilution gas with the mixture. This is preferable because coexistence of an inorganic gas enables the method to be further enhanced in selectivity of separation and permeation rate of a straight-chain conjugate diene.

The inorganic gas may be one or more types selected from helium, argon, nitrogen, hydrogen, carbon monoxide, carbon dioxide and oxygen.

The mix ratio of the mixture containing a straight-chain conjugate diene and a straight-chain olefin and the inorganic gas, i.e., the mixture:the inorganic gas is preferably 20 to 99 mol %:80 to 1 mol %, more preferably 30 to 95 mol %:70 to 5 mol %, more preferably 40 to 90 mol %:60 to 10 mol %. The inorganic gas contained in an amount of 1 mol % or more and 80 mol % or less is preferable because the selectivity of separation and permeation rate of the straight-chain conjugate diene can be enhanced.

The method for separating a straight-chain conjugate diene according to the present invention intends to separate the straight-chain conjugate diene from other components with the pores and adsorptivity of a zeolite.

That is, the present invention enables a straight-chain conjugate diene to be selectively separated by including an alkali metal in a zeolite to change the pore diameter and static electric field of the zeolite to adjust the molecular sieve action and adsorptivity thereof.

Separation of a straight-chain conjugate diene with a zeolite membrane complex according to the present invention is carried out at a temperature of preferably 20 to 100° C., more preferably 35 to 65° C. When the separation is carried out at a temperature of lower than 20° C., the permeability of the complex would be decreased while the separation is carried out at a temperature of higher than 100° C., pores of the composite would be clogged due to polymerization of the conjugated diene.

The zeolite membrane composite used in the present invention has a permeability and a separation coefficient that are industrially enabled.

The permeability and separation coefficient were obtained using 1,3-butadiene and 1-butene under a condition where the zeolite membrane composite is at a temperature of 60° C. in accordance with a vapor permeation (VP) test.

The permeability and separation coefficient can be measured under the conditions described below using a vapor permeation apparatus schematically shown in FIG. 1.

Herein, the separation coefficient of 1,3-butadiene/1-butene is used as a separation coefficient indicating the separation capability of the zeolite membrane complex used in the present invention. The separation coefficient of 1,3-butadiene/1-butene refers to a ratio of the ratio of the 1,3-butadiene concentration ($P_{butadiene}$, mol %) and the 1-butene concentration ($P_{butene}$, mol %) in the permeated gas to the ratio of the 1,3-butadiene concentration ($S_{butadiene}$, mol %) and the 1-butene concentration ($S_{butene}$, mol %) in the supplied gas.

$$\text{Separation coefficient} = (P_{butadiene}/P_{butene})/(S_{butadiene}/S_{butene})$$

The 1,3-butadiene permeability of the zeolite membrane composite at 60° C. is preferably $3.0 \times 10^{-9}$ mol·m$^{-2}$·s$^{-1}$·Pa$^{-1}$ or greater, more preferably $7.0 \times 10^{-9}$ mol·m$^{-2}$·s$^{-1}$·Pa$^{-1}$ or greater. If the permeability is smaller than $3.0 \times 10^{-9}$ mol·m$^{-2}$·s$^{-1}$·Pa$^{-1}$, the separation facility might be enormous.

The 1,3-butadiene/1-butene separation coefficient of the zeolite membrane composite at 60° C. is preferably 1.4 or greater, more preferably 2.5 or greater. If the 1,3-butadiene/1-butene separation coefficient is smaller than 1.4, the concentration of the conjugate diene in the permeated liquid is not increased and thus the separation efficiency might not be sufficient.

The permeability and separation coefficient were determined in the following manners.

In FIG. 1, a mixed fluid the supplied amount of 1,3-butadiene and 1-butene gases of which were controlled with a mass flow controller (not shown) was supplied to a separation cell which was heated with a heater and retained at an atmospheric pressure. The separation cell is structured so that the mixed fluid to be separated is supplied onto the outer surface of a cylindrical zeolite membrane complex and the permeated gas is taken from the inner surface. The total feed rate of the mixed gas to be supplied was 200 ml/min and the ratio of 1,3-butadiene and 1-butene (molar ratio=partial pressure ratio) was 1:1 or 4:1. Helium gas was flowed as a carrier gas to the permeated side at a flow rate of 200 mL/min. The recovery gas containing the gas having permeated through the zeolite membrane was sampled and analyzed with gas chromatograph to calculate the permeability (mol·m$^{-2}$·s$^{-1}$·Pa$^{-1}$) and separation coefficient of the gas having permeated through the zeolite membrane.

EXAMPLES

The present invention will be described in more detail below with reference to the following examples but are not limited thereto.

(Measurement of Particle Size Distribution of Seed Crystal)

The particle size distribution of seed crystals was measured under the following conditions.

Apparatus name: Laser Diffraction Particle Size Analyzer LA-500
Measuring method: Use of Fraunhofer diffraction theory and Mie scattering theory in combination
Measurement range: 0.1 to 200 μm
Light source: He—Ne laser (632.8 nm)
Detector: ring-shaped silicon photo diode
Dispersion solvent: water The dispersion liquid for measuring the particle size distribution of seed crystals was prepared by putting water in an ultrasonic dispersion bath of a measuring apparatus and then adding seed crystals in the water while being stirred so that the resulting dispersion liquid was circulated in a flow cell and the intensity of light permeating through the dispersion liquid was within the adequate light intensity indicated on the apparatus. Whereupon, the amount of water that is the dispersion solvent is usually 250 ml and the amount of the seed crystals to be dispersed is usually 0.01 g. After the seed crystals were added, ultrasonic wave is applied for 10 minutes to the dispersion liquid to break up the agglomerated seed crystal therein, and then the particle size distribution was measured by a flow method. In the resulting cumulative distribution chart (volume basis, integrated from the smallest particle size), the diameter providing a height at 50% (median diameter) was made D50 (average particle diameter).

(Measurement of Pore Distribution of Porous Support by Mercury Intrusion Method)

The pore distribution of a porous support was determined from an intrusion curve obtained by a mercury intrusion method in the range of 3.7 kPa (corresponding to a pore diameter of 404 μm) and 414 MPA (corresponding to a pore diameter of 0.0036 μm) after subjecting the support to a decompression treatment under reduced pressure (50 μmHg or lower) for 10 minutes. From the resulting intrusion curve obtained by the mercury intrusion method, D50 (pore diameter at a point when the total pore volume derived by integration from the largest pore diameter reaches 50 percent of the whole pore volume) was determined and defined as average pore diameter.

Example 1

(a) Preparation of Porous Support with Seed Crystal Attached Thereto

A seed crystal that is a commercially available USY zeolite powder (Si/Al=7, manufactured by Tosoh Corporation) was prepared and wet-milled with a ball mill. The average particle diameter of the USY zeolite after milled was measured and found to be 200 nm. Addition of water to the milled USY zeolite was followed by stirring and centrifugal separation at 4,000 rpm for 10 minutes. After supernatant was skimmed, seed crystal slurry 1 was prepared so that the concentration of the seed crystal therein was 2.5 g/L. Next, a cylindrical α-alumina support with a 1 cm diameter and a 3 cm length was prepared as a porous support. The average pore diameter and porosity of the support were 150 nm and 37%, respectively. The α-alumina support was immersed in the seed crystal slurry for 3 minutes thereby producing seed crystal-attached porous support 1. The amount of the seed crystal supported on the porous support 1 was measured and found to be 2.2 mg, and observation of the surface and cross-section of the porous support with, SEM revealed that the seed crystal was mainly supported on the support.

(b) Formation of Zeolite Membrane

Aqueous solutions of sodium silicate, sodium hydroxide and aluminum hydroxide were mixed and then aged at a temperature of 70° C. for 5 minutes thereby producing a synthetic aluminosilicate gel. The composition of the gel by molar ratio was $Na_2O:Al_2O_3:SiO_2:H_2O=80:1:9:5000$. Seed crystal-attached porous support 1 was immersed in the resulting synthetic aluminosilicate gel and then hydrothermally synthesized at a temperature of 70° C. for 24 hours thereby producing Na zeolite membrane complex 1. Na zeolite membrane complex 1 was a NaX-type zeolite and had a Na ratio therein of 13.6 percent by mass. The Na amount in the zeolite was calculated from the Si/Al ratio in the skeleton measured using XRD. The structure of the zeolite was determined from the peak pattern in the XRD measurement.

Example 2

Na zeolite membrane complex 1 produced in the same manner as Example 1 was immersed in an aqueous solution of 0.01 M of rubidium nitrate under reduced pressure for one hour and then washed repeatedly with distilled water and dried at room temperature under reduced pressure thereby producing a Rb zeolite membrane complex. The resulting Rb zeolite membrane complex is a Rb—Na complex X-type zeolite, and the ratios of Rb and Na in the zeolite were 8.75 percent by mass and 10.3 percent by mass, respectively, and the molar ratio of Rb and Na was Rb/Na=0.23 mol/mol. The amount of Rb in the zeolite was calculated from the Na concentration in the rubidium nitrate aqueous solution measured using ICP after cation exchange.

Example 3

Na zeolite membrane complex 1 produced in the same manner as Example 1 was immersed in an aqueous solution of 0.01 M of cesium nitrate under reduced pressure for one hour and then washed repeatedly with distilled water and dried at room temperature under reduced pressure thereby producing Cs zeolite membrane complex 1. The resulting Cs zeolite membrane complex 1 is a Cs—Na complex X-type zeolite, and the ratios of Cs and Na in the zeolite were 11.5 percent by mass and 10.3 percent by mass, respectively, and the molar ratio of Cs and Na was Cs/Na=0.19 mol/mol. The amount of Cs in the zeolite was calculated from the Na concentration in the cesium nitrate aqueous solution measured using ICP after cation exchange.

Example 4

Na zeolite membrane complex 1 produced in the same manner as Example 1 was immersed in an aqueous solution of 0.01 M of potassium nitrate under reduced pressure for one hour and then washed repeatedly with distilled water and dried at room temperature under reduced pressure thereby producing a K zeolite membrane complex. The resulting K zeolite membrane complex is a K X-type zeolite, and the ratio of K in the zeolite was 17.2 percent by mass. The amount of K in the zeolite was calculated from the Na concentration in the potassium nitrate aqueous solution measured using ICP after cation exchange.

Example 5

(a) Preparation of Porous Support with Seed Crystal Attached Thereto

A seed crystal-attached porous support was prepared using ZSM-5 zeolite powder (manufactured by Tosoh Corporation) in accordance with the method of Example 1.

(b) Formation of Zeolite Membrane

Colloidal silica ($SiO_2$: 30.6 percent by mass, $Na_2O$: 0.42 percent by mass, $H_2O$: 69 percent by mass), sodium hydroxide, aluminum hydroxide and distilled water were mixed and then aged at a temperature of 50° C. for 248 minutes thereby producing a synthetic aluminosilicate gel. The composition of the gel by molar ratio was $Na_2O:Al_2O_3:SiO_2:H_2O=8:0.15:36:1200$. The seed crystal-attached porous support produced above was immersed in the resulting synthetic aluminosilicate gel and then hydrothermally synthesized at a temperature of 180° C. for 12 hours thereby producing Na zeolite membrane complex 2. Na zeolite membrane complex 2 was NaZSM-5-type zeolite. The structure of the zeolite was determined from the peak pattern in the XRD measurement.

The resulting Na zeolite membrane complex 2 was immersed in an aqueous solution of 0.01 M of cesium chloride at a temperature of 90° C. for one hour and then washed repeatedly with distilled water and dried at a temperature of 110° C. thereby producing Cs zeolite membrane complex 2. The resulting Cs zeolite membrane complex 2 was Cs-ZSM-5-type zeolite, the ratio of Cs therein was 11.6 percent by mass. The amount of Cs in the zeolite was calculated from the change in weight of the zeolite before and after cation exchange.

Comparative Example 1

Na zeolite membrane complex 1 produced in the same manner as Example 1 was immersed in an aqueous solution of 0.01 M of silver nitrate under reduced pressure for one hour and then washed repeatedly with distilled water and dried at room temperature under reduced pressure thereby producing an Ag zeolite membrane complex. The resulting Ag zeolite membrane complex is an Ag X-type zeolite, and the ratio of Ag in the zeolite was 58.4 percent by mass. The amount of Ag in the zeolite was calculated from the difference in the membrane weight before and after cation exchange.

Comparative Example 2

Na zeolite membrane complex 1 produced in the same manner as Example 1 was immersed in an aqueous solution of 0.01 M of magnesium nitrate hexahydrate under reduced pressure for one hour and then washed repeatedly with distilled water and dried at room temperature under reduced pressure thereby producing a Mg zeolite membrane complex. The resulting Mg zeolite membrane complex is a Mg X-type zeolite.

Comparative Example 3

Na zeolite membrane complex 1 produced in the same manner as Example 1 was immersed in an aqueous solution of 0.01 M of calcium chloride dihydrate under reduced pressure for one hour and then washed repeatedly with distilled water and dried at room temperature under reduced pressure thereby producing a Ca zeolite membrane complex. The resulting Ca zeolite membrane complex is a Ca X-type zeolite.

Comparative Example 4

Na zeolite membrane complex 1 produced in the same manner as Example 1 was immersed in an aqueous solution of 0.01 M of strontium nitrate under reduced pressure for one hour and then washed repeatedly with distilled water and dried at room temperature under reduced pressure thereby producing a Sr zeolite membrane complex. The resulting Sr zeolite membrane complex is a Sr X-type zeolite.

Comparative Example 5

Na zeolite membrane complex 1 produced in the same manner as Example 1 was immersed in an aqueous solution of 0.01 M of barium nitrate under reduced pressure for one hour and then washed repeatedly with distilled water and dried at room temperature under reduced pressure thereby producing a Ba zeolite membrane complex. The resulting Ba zeolite membrane complex is a Ba X-type zeolite.

Comparative Example 6

(a) Preparation of Seed Crystal

Sodium hydroxide, tetraethyl orthosilicate (TEOS), tetrapropylammonium hydroxide (TPAOH) and pure water were mixed and stirred at room temperature for 24 hours thereby producing a synthetic solution. The composition of the solution was $0.004Na_2O:SiO_2:0.176TPAOH:43.9H_2O$. The resulting synthesized solution was hydrothermally synthesized under a condition of stirring at a temperature of 100° C. for 24 hours. After the synthesis, the solution was filtrated and the collected powder was calcined at a temperature of 530° C. for 8 hours thereby producing silicalite-1 seed crystal.

(b) Preparation of Seed Crystal-Attached Porous Support

Silicalite-1 powder prepared as a seed crystal was dispersed in pure water so that the concentration of the seed crystal in the slurry was 10 g/L thereby preparing a seed crystal suspension. Next, a cylindrical α-alumina support with a 1 cm diameter and a 3 cm length was prepared as a porous support. The average pore diameter and porosity of the support were 150 nm and 37%, respectively. The α-alumina support was immersed in the seed crystal suspension for one minute thereby producing a seed crystal-attached porous support. The amount of the seed crystal supported on the porous support was measured and found to be 5.6 mg, and observation of the surface and cross-section of the porous support with SEM revealed that the seed crystal was mainly supported on the support.

(c) Formation of Zeolite Membrane

Tetraethyl orthosilicate (TEOS), tetrapropylammonium hydroxide (TPAOH), ethanol and pure water were mixed and aged at a temperature of 60° C. for 4 hours thereby producing a synthetic solution. The composition of the solution was $SiO_2:0.12TPAOH:66H_2O:8EtOH$. The seed crystal-attached porous support was immersed in the resulting synthesized solution and hydrothermally synthesized at a temperature of 100° C. for 7 days, and then calcined at a temperature of 500° C. for 8 hours thereby producing silicalite-1 zeolite membrane complex. After the support was calcined by increasing the temperature at a rate of 1° C./min and retained at a temperature of 500° C. for 8 hours, the temperature was decreased at a rate of 1° C./min. The zeolite structure of the resulting zeolite membrane complex was determined as silicalite-1 from the peak pattern measured with XRD.

Examples 6 to 11 and Comparative Examples 7 to 12

A vapor permeation test was carried out using Na zeolite membrane composite 1, Rb zeolite membrane composite, Cs zeolite membrane composite 1, K zeolite membrane composite, and Cs zeolite membrane composite 2 produced in Examples 1 to 5 and Ag zeolite membrane composite, Mg zeolite membrane composite, Ca zeolite membrane composite, Sr zeolite membrane composite, Ba zeolite membrane composite, and silicalite-1 zeolite membrane composite produced in Comparative Examples 1 to 6 and an apparatus schematically shown in FIG. 1. The results are set forth in Tables 1 to 4 below.

Examples 12 to 15

A vapor permeation test was carried out using Cs zeolite membrane complex 1 of Example 3 and a raw gas (a mixture of 80 mol % of 1,3-butadiene and 20 mol % of 1-butene) blended with an inorganic gas (He) as dilution gas with variation of the total pressure of the raw gas within the combined pressure of the raw gas and inorganic gas of 101 kPa. The results are set forth in Table 5 below.

As apparent from the results, it is found that coexistence of the inorganic gas with the raw gas enables the butadiene permeability and separation coefficient to be enhanced.

Example 16

A sodium silicate solution, a sodium hydroxide aqueous solution and a mixed solution of sodium hydroxide and aluminum hydroxide were charged into three layers in the order as stated into a vessel so that the solutions were not mixed and stirred at 2000 rpm with an ultra-stirrer for 5 minutes. The mixture was then aged at a temperature of 25° C. for 4 hours thereby producing a synthetic aluminosilicate gel. The composition of the gel by molar ratio was $Na_2O:Al_2O_3:SiO_2:H_2O=22:1:25:990$. Seed crystal-attached porous support 1 was immersed in the resulting synthesized aluminosilicate gel and hydrothermally synthesized while being stirred at a rate of 15 rpm and a temperature of 100° C. for 4 hours thereby producing Na zeolite membrane complex 3. Na zeolite membrane complex 3 was a Na Y-type zeolite and the ratio of Na therein was 12.0 percent by mass. The Na amount in the zeolite was calculated from the Si/Al ratio in the skeleton measured using XRD. The structure of the zeolite was determined from the peak pattern in the XRD measurement.

Example 17

Na zeolite membrane complex 3 produced in the same manner as Example 16 was immersed in an aqueous solution of 0.01 M of cesium nitrate for one hour and then washed repeatedly with distilled water and dried at a temperature of 70° C. thereby producing Cs zeolite membrane complex 3. The resulting Cs zeolite membrane complex 3 was a Cs—Na complex Y-type zeolite, and the molar ratio of Cs and Na was Cs/Na=0.23 mol/mol. The amount of Cs in the zeolite was calculated from the change in weight of the zeolite before and after cation exchange.

Examples 18 and 19

A vapor permeation test was carried out using Na zeolite membrane composite 3 and Cs zeolite membrane composite 3 produced in Examples 16 and 17. The results are set forth in Table 6.

As apparent from the results, the Y-type zeolite was found to be superior in butadiene permeability and separation coefficient to the X-type zeolite.

Example 20

Cs zeolite membrane composite 4 was produced in the same manner as Example 17 except that the concentration of cesium nitrate was changed to 0.05 M. The resulting Cs zeolite membrane composite 4 was a Cs—Na composite Y-type zeolite, and the molar ratio of Cs and Na was Cs/Na=0.32 mol/mol. The amount of Cs in the zeolite was calculated from the Na concentration in the cesium nitrate aqueous solution measured using ICP after cation exchange.

Example 21

Cs zeolite membrane composite 5 was produced in the same manner as Example 17 except that the concentration of cesium nitrate was changed to 0.1 M. The resulting Cs zeolite membrane composite 5 was a Cs—Na composite Y-type zeolite, and the molar ratio of Cs and Na was Cs/Na=0.56 mol/mol. The amount of Cs in the zeolite was calculated from the Na concentration in the cesium nitrate aqueous solution measured using ICP after cation exchange.

Example 22

Cs zeolite membrane composite 6 was produced in the same manner as Example 17 except that the concentration of cesium nitrate was changed to 0.5 M. The resulting Cs zeolite membrane composite 6 was a Cs—Na composite Y-type zeolite, and the molar ratio of Cs and Na was Cs/Na=1.44 mol/mol. The amount of Cs in the zeolite was calculated from the Na concentration in the cesium nitrate aqueous solution measured using ICP after cation exchange.

Examples 23 to 25

A vapor permeation test was carried out using Cs zeolite membrane composites 4 to 6 produced in Examples 20 to 22. The results are set forth in Table 7 below.

As apparent from the results, the Cs—Na Y-type zeolites having a Cs/Na molar ratio of 0.1 to 1.5 mol/mol are extremely excellent in butadiene permeability and separation coefficient. However, it is also found that when the Cs/Na molar ratio as shown in Example 25 exceeds 0.6 mol/mol, the composite is degraded in butadiene permeability though it is larger in separation coefficient than the Na Y-type zeolite of Example 18.

In FIG. 1, a mixed fluid the supplied amount of 1,3-butadiene and 1-butene gases of which were controlled with a mass flow controller (not shown) was supplied to a separation cell which was heated with a heater and retained at an atmospheric pressure. The separation cell is structured so that the mixed fluid to be separated is supplied onto the outer surface of a cylindrical zeolite membrane complex and the permeated gas is taken from the inner surface. The total feed rate of a mix gas to be supplied was fixed to 200 ml/min, and the ratio of 1,3-butadiene and 1-butene gases was altered depending on Examples and Comparative Examples. Furthermore, helium gas was supplied as gas for diluting the raw gas depending on Examples. Helium gas was flowed as a carrier gas to the permeated side at a flow rate of 200 mL/min. The recovery gas containing the gas having permeated through the zeolite membrane was sampled and analyzed with gas chromatograph and evaluated by calculating the permeability ($mol \cdot m^{-2} \cdot s^{-1} \cdot Pa^{-1}$) and separation coefficient of the gas having permeated through the zeolite membrane. The results are set forth in Tables 1 to 4 below. The separation coefficient denotes a ratio of the ratio of the 1,3-butadiene concentration ($P_{butadiene}$, mol %) and the 1-butene concentration ($P_{butene}$, mol %) in the permeated gas to the ratio of the 1,3-butadiene concentration ($S_{butadiene}$, mol %) and the 1-butene concentration ($S_{butene}$, mol %) in the supplied gas as represented by the following formula.

Separation coefficient=$(P_{butadiene}/P_{butene})/(S_{butadiene}/S_{butene})$

From the permeability and separation coefficient of each of Examples and each of Comparative Examples, a membrane area to obtain a butadiene purity of 95% was determined from a simulation, and when the required membrane area of Example 7 was 100, the relative area of each of Examples and Comparative Examples required to obtain the 95% purity were set forth in Tables 2, 3 and 4 below.

TABLE 1

|  | Example 6 | Comparative Example 7 |
|---|---|---|
| Zeolite membrane composite | Na Zeolite membrane composite 1 | Ag Zeolite membrane composite |
| Zeolite | NaX | AgX |
| Metal content in zeolite, mass % | Na 13.6 | Ag 58.4 |
| Temperature ° C. | 40 | |
| Supplied partial pressure, 1,3-butadiene (kpa)/1-butene (kpa) | 50/50 | |
| Butadiene permeability, $10^{-9}$ mol · $m^{-2}$ · $s^{-1}$ · $Pa^{-1}$ | 2.9 | 0.7 |
| Separation coefficient | 3.20 | 1.20 |

TABLE 2

|  | Example 7 | Example 8 | Example 9 | Example 10 |
|---|---|---|---|---|
| Zeolite membrane composite | Na Zeolite membrane composite1 | Rb Zeolite membrane composite | Cs Zeolite membrane composite 1 | K zeolite membrane composite |
| Zeolite | NaX | Rb—NaX | Cs—NaX | KX |
| Metal content in zeolite, mass % | Na 13.6 | Rb 8.75 Na 10.3 | Cs 11.5 Na 10.3 | K 17.2 |
| Temperature ° C. | 60 | | | |
| Supplied partial pressure, 1,3-butadiene (kpa)/1-butene (kpa) | 80/20 | | | |
| Butadiene permeability, $10^{-9}$ mol · $m^{-2}$ · $s^{-1}$ · $Pa^{-1}$ | 7.7 | 45.6 | 33.9 | 23.9 |
| Separation coefficient | 1.86 | 1.80 | 2.63 | 1.45 |
| Relative membrane area to obtain 95% or more butadiene purity against that of Example 7 being 100 (calculated value) | 100 | 17 | 16 | 53 |

TABLE 3

|  | Comparative Example 8 | Comparative Example 9 | Comparative Example 10 | Comparative Example 11 |
|---|---|---|---|---|
| Zeolite membrane composite | Mg zeolite membrane composite | Ca zeolite membrane composite | Sr zeolite membrane composite | Ba zeolite membrane composite |

TABLE 3-continued

|  | Comparative Example 8 | Comparative Example 9 | Comparative Example 10 | Comparative Example 11 |
|---|---|---|---|---|
| Zeolite | MgX | CaX | SrX | BaX |
| Temperature °C. | | 60 | | |
| Supplied partial pressure, 1,3-butadiene (kpa)/1-butene (kpa) | | 80/20 | | |
| Butadiene permeability, $10^{-9}$ mol · m$^{-2}$ · s$^{-1}$ · Pa$^{-1}$ | 8.0 | 15.0 | 4.8 | 6.3 |
| Separation coefficient | 1.08 | 1.00 | 1.11 | 1.06 |
| Relative membrane area to obtain 95% or more butadiene purity against that of Example 7 being 100 | 805 | No Purification capability | 942 | 1,186 |

TABLE 4

|  | Example 11 | Comparative Example 12 |
|---|---|---|
| Zeolite membrane composite | Cs Zeolite membrane composite2 | silicalite-1Zeolite membrane composite |
| Zeolite | Cs-ZSM-5 | silicalite-1 |
| Metal content in zeolite mass % | Cs 11.6 | — |
| Temperature °C. | 60 | |
| Supplied partial pressure, 1,3-butadiene (kpa)/1-butene (kpa) | 80/20 | |
| Butadiene permeability, $10^{-9}$ mol · m$^{-2}$ · s$^{-1}$ · Pa$^{-1}$ | 4.4 | 444 |
| Separation coefficient | 1.58 | 1.10 |
| Relative membrane area to obtain 95% or more butadiene purity against that of Example 7 being 100 | 231 | 112 |

TABLE 5

|  | Example 12 | Example 13 | Example 14 | Example 15 |
|---|---|---|---|---|
| Zeolite membrane composite | Cs zeolite membrane composite 1 | | | |
| Zeolite | Cs—NaX | | | |
| Metal content in zeolite mass % | Cs 11.5 Na 10.3 | | | |
| Temperature °C. | 40 | | | |
| Raw material molar fraction, 1,3-butadiene/1-butene | 80/20 | | | |
| Raw material total pressure, kpa | 101 | 76 | 51 | 25 |
| Inorganic gas | He | | | |
| Butadiene permeability, $10^{-9}$ mol · m$^{-2}$ · s$^{-1}$ · Pa$^{-1}$ | 31.2 | 49.4 | 84.2 | 168.0 |
| Separation coefficient | 3.50 | 4.09 | 4.70 | 4.86 |

TABLE 6

|  | Example 18 | Example 19 |
|---|---|---|
| Zeolite membrane composite | Na zeolite membrane composite 3 | Cs zeolite membrane composite 3 |
| Zeolite | NaY | Cs—NaY |
| Metal ion (molar fraction) | Na | Cs (0.19), Na (0.81) |
| Temperature °C. | 60 | |
| Supplied partial pressure, 1,3-butadiene (kpa)/1-butene (kpa) | 80/20 | |
| Butadiene permeability, $10^{-9}$ mol · m$^{-2}$ · s$^{-1}$ · Pa$^{-1}$ | 56.5 | 49.5 |
| Separation coefficient | 2.55 | 3.53 |

TABLE 7

|  | Example 23 | Example 24 | Example 25 |
|---|---|---|---|
| Zeolite membrane composite | Cs zeolite membrane composite 4 | Cs zeolite membrane composite 5 | Cs zeolite membrane composite 6 |
| Zeolite | Cs-NaY | | |
| Metal ion (molar fraction) | Cs (0.24), Na (0.76) | Cs (0.36), Na (0.64) | Cs (0.59), Na (0.41) |
| Temperature °C. | 60 | | |
| Supplied partial pressure, 1,3-butadiene (kpa)/1-butene (kpa) | 80/20 | | |
| Butadiene permeability, $10^{-9}$ mol · m$^{-2}$ · s$^{-1}$ · Pa$^{-1}$ | 48.0 | 48.8 | 12.7 |
| Separation coefficient | 4.20 | 3.88 | 3.86 |

INDUSTRIAL APPLICABILITY

The separation method according to the present invention can separate selectively a straight-straight conjugated diene at a high purity from a mixture containing the straight-straight conjugated diene and thus are industrially useful. In particular, the present invention can easily separate a straight-straight conjugated diene selectively in a high purity from a mixture of a straight-chain conjugated diene and a straight-chain olefin and thus significantly useful.

The invention claimed is:

1. A method for separating a straight-chain conjugated diene comprising separating the straight-chain conjugated diene from a mixture of the straight-chain conjugated diene and at least one type of straight-chain olefin using a zeolite membrane composite comprising a porous support and a zeolite layer formed on the surface and in fine pores of the support wherein the zeolite comprises an alkali metal as a cation.

2. The method for separating a straight-chain conjugated diene according to claim 1 wherein the zeolite comprises a faujasite type zeolite.

3. The method for separating a straight-chain conjugated diene according to claim 1 wherein the alkali metal is at least one type selected from Na, K, Rb and Cs.

4. The method for separating a straight-chain conjugated diene according to claim 1 wherein the alkali metal consists of Na and Cs.

5. The method for separating a straight-chain conjugated diene according to claim 1 wherein the Cs/Na molar ratio of the alkali metal is from 0.1 to 1.5 mol/mol.

6. The method for separating a straight-chain conjugated diene according to claim 1 wherein the straight-chain conjugated diene is butadiene.

7. The method for separating a straight-chain conjugated diene according to claim 1 wherein the zeolite membrane composite has a 1,3-butadine/1-butene separation coefficient of 1.4 or greater at 60° C.

8. The method for separating a straight-chain conjugated diene according to claim 1 wherein the faujasite type zeolite is a Y-type zeolite.

9. The method for separating a straight-chain conjugated diene according to claim 1 wherein the separation is carried out in coexistence of an inorganic gas with the mixture.

10. The method for separating a straight-chain conjugated diene according to claim 9 wherein the inorganic gas is at least one type selected from helium, argon, nitrogen, hydrogen, carbon monoxide, carbon dioxide and oxygen.

* * * * *